United States Patent [19]

Hvid

[11] Patent Number: Plant 6,179

[45] Date of Patent: May 17, 1988

[54] BEGONIA PLANT NAMED JANE

[75] Inventor: Soeren Hvid, Aarup, Denmark

[73] Assignee: L. Daehnfeldt A/S, Odense, Denmark

[21] Appl. No.: 838,072

[22] Filed: Mar. 10, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Olson and Olson

[57] ABSTRACT

A new and distinctive cultivar of begonia plant bearing fully-filled flowers in a nice rose color against a compact background of small leaves with a reddish green color. The plant is characterized by vigorous and floriferous growth, producing flowers and leaves of long persistence, excellent display, and excellent keeping qualities.

1 Drawing Sheet

BACKGROUND OF THE INVENTION

This invention relates to a new and distinctive cultivar of begonia plant known botanically as *Begonia hiemalis* Begonia (Fotsch) and known by the cultivar name Jane.

This new cultivar was discovered by me as a seedling from a controlled crossing of *Begonia tuberous* hybrida seedling as the seed parent with *Begonia socotrana* as the pollen parent.

Asexual reproduction by stem and/or leaf cuttings has reproduced the unique features of the new cultivar through successive propagations.

The following characteristics distinguish the new begonia from both its parents and other begonias commercially known and used in the floriculture industry:

(1) The new cultivar shows pubscense on the foliage. The plant form is vigorous and compact.

(2) The flowers of Jane are medium sized and fully-filled, in a nice attractive rose color.

(3) The foliage of Jane has a green color with a shade of red on the small sized leaves.

(4) The new cultivar is considered to be highly floriferous. The stems on which flowering occurs tend to have initiation and development at several nodes at one time.

(5) The keeping qualities of the flowers and the foliage in all seasons allows production and sales efficiencies to be maximized.

(6) The new cultivar tends to be very vigorous so that 10 cm. (4 inch) pot production is best done with shoot cuttings and tip pinching.

(7) Propagation by leaf cuttings is difficult under light and high temperatures in summer months. Stem cuttings can readily be produced in this season.

(8) The flowers of Jane undergo little or no fading under abnormal conditions. Bavaria is also very superior with respect to keeping qualities of winter crops of hiemalis begonias.

THE DRAWING

The accompanying color photograph illustrates the overall appearance of this cultivar taken as a face view of the plant and showing the colors as true as it is reasonably possible to obtain in a colored reproduction of this type.

DESCRIPTION OF THE NEW VARIETY

The following is a detailed description of my new begonia cultivar based on plants produced under commercial practices in glasshouses in various places in Denmark, Color references are made to The Royal Horticultural Society Colour Chart, except where general color terms of ordinary dictionary significance are used.

Parentage: A controlled cross of *Begonia tuberous* hybrida and *Begonia socotrana.*

Propagation:

*Type cutting.*—Stem cutting.

*Time to root.*—27–30 days at 21° C. in summer; 25–28 days at 21° C. in winter.

*Rooting habit.*—Uniform, dentritic, fibrous.

*Time for shoot development of leaf cuttings.*—70–85 days to develop adventitious shoots 5–6 cm. (1.96–2.37 inches) long from stick date.

THE PLANT

Form: Low compact bush type, self branching with a compact growth, herbaceous.

Habit of growth: Generally rapid, vigorous with strong stems, strong penduncles and strong pedicles.

Foliage: Leaves simple, alternate, borne on vigorous petioles, firm.

(1) *Size.*—Small leaves at maturity from 5–6 cm (1.97–2.4 inches) leaves may be smaller or bigger depending on density of leaf canopy.

(2) *Shape.*—Ovate, slightly concave.

(3) *Texture.*—Leaf is firm, top glabrous, underside rugose.

(4) *Margin.*—Crenate.

(5) *Color.*—Young foliage top side; medium green, under side; medium green to light green, mature foliage top side; medium green with a slight red infusion, under side; light green.

(6) *Veination.*—Palmate.

THE FLOWER

Flowering habits: Flowering in racemes, with several clusters arising from the stem nodes at the same time giving a highly floriferous appearance. Flowering is continuous for a long period of time.

Natural flowering season: Flowering occurs naturally with shortened days lengths beginning mid-September and continuing through May.

Flower bud: Flat, oval, and nearly round.

Flowers borne: On vigorous penduncles and pedicles in a raceme. The extra doubleness of the flowers causes a pendulous appearance because of the weight of the flowers.

Quantity: Very floriferous, often having 18–20 flowers per main stem in flowering stage at one time.

Tepals:

(1) *Shape.*—Nearly circular.

(2) *Color.*—Top side in winter when opening: light rose HCC 618/1. fading to: rose HCC 523/1. under side: rose HCC 523/1.

(3) *Number.*—16–32.

(4) *Size.*—Basal from 25 mm (1.0 inch), interior tepals 10–20 mm (0.4–0.8 inch).

(5) *Flower size.*—Up to 5 cm (2 inches) in diameter.

Reproductive organs:

*Stamens.*—None; cultivar is sterile.

Disease resistance: No particular increase in resistance to disease observed to date.

I claim:

1. A new and distinct cultivar of *Begonia hiemalis* plant named Jane, as shown and described, and particularly characterized by its compact growth, small leaves with a reddish green color and fully filled flowers in a nice rose color; floriferous habit and by its excellent keeping qualities.

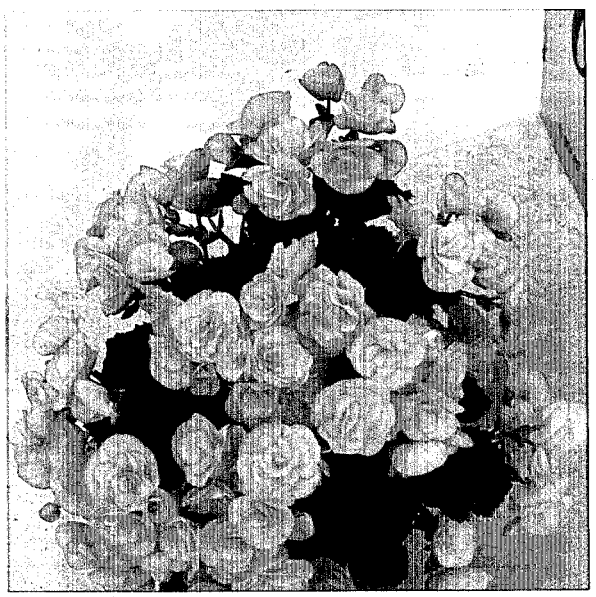

* * * * *